(12) United States Patent
Lalam et al.

(10) Patent No.: US 12,313,540 B2
(45) Date of Patent: May 27, 2025

(54) SIMULTANEOUS ULTRASONIC VIBRATION AND GAS SENSING BASED ON A TUNABLE FIBER RING LASER

(71) Applicant: United States Department of Energy, Washington, DC (US)

(72) Inventors: Nageswara Rao Lalam, Pittsburgh, PA (US); Michael P. Buric, Fairview, WV (US); Ping Lu, West Hartford, CT (US); Fei Lu, Lubbock, TX (US); Tao Hong, Xi'an (CN); Ruishu Feng Wright, Pittsburgh, PA (US)

(73) Assignee: United States Department of Energy, Washington, DC (US)

( * ) Notice: Subject to any disclaimer, the term of this patent is extended or adjusted under 35 U.S.C. 154(b) by 313 days.

(21) Appl. No.: 17/967,025

(22) Filed: Oct. 17, 2022

(65) Prior Publication Data
US 2023/0125056 A1  Apr. 20, 2023

Related U.S. Application Data

(60) Provisional application No. 63/257,488, filed on Oct. 19, 2021.

(51) Int. Cl.
*G01N 21/39* (2006.01)
*G01N 21/17* (2006.01)
(Continued)

(52) U.S. Cl.
CPC ......... *G01N 21/39* (2013.01); *G01N 33/0036* (2013.01); *H01S 3/06791* (2013.01);
(Continued)

(58) Field of Classification Search
CPC ............... G01N 21/39; G01N 33/0036; G01N 2021/1704; G01N 2021/458;
(Continued)

(56) References Cited

U.S. PATENT DOCUMENTS 9,891,166 B2    2/2018  Wild et al.
2009/0129721 A1*  5/2009  Chen .................. G01N 21/7703
                                                                        385/12
(Continued)

FOREIGN PATENT DOCUMENTS

CN      109100008 A  * 12/2018  ............... G01H 9/00
CN      112838466 A  *  5/2021  ............. H01S 3/067
(Continued)

OTHER PUBLICATIONS

Z. Liu, X. Zhang, Z. Gong, Y. Zhang and W. Peng, "Fiber Ring Laser-Based Displacement Sensor," in IEEE Photonics Technology Letters, vol. 28, No. 16, pp. 1723-1726, 15 Aug. 15, 2016.
(Continued)

*Primary Examiner* — Md M Rahman
(74) *Attorney, Agent, or Firm* — Aaron R. Keith; Michael J. Dobbs

(57) ABSTRACT

One or more embodiments relates to a system for simultaneously detecting vibration and the presence of a target gas having a tunable fiber ring laser in electronic and optical communication with a vibration sensor and a gas detection sensor. One or more embodiments relate to a method for simultaneously measuring vibration and detecting the presence of a target gas in an environment having the steps of providing a system for simultaneously measuring vibration and detecting a target gas into an environment; sending an optical signal to a vibration sensor and gas detection sensor; and collecting and analyzing modified signals from the vibration sensor and gas detection sensor.

5 Claims, 18 Drawing Sheets

(51) Int. Cl.
  *G01N 21/45* (2006.01)
  *G01N 33/00* (2006.01)
  *H01S 3/067* (2006.01)
(52) U.S. Cl.
  CPC ............... *G01N 2021/1704* (2013.01); *G01N 2021/458* (2013.01); *G01N 2201/06113* (2013.01); *G01N 2201/0873* (2013.01)
(58) Field of Classification Search
  CPC . G01N 2201/06113; G01N 2201/0873; G01N 21/3504; H01S 3/06791; H01S 3/0014; H01S 3/06708; H01S 3/1067; H01S 3/06712; H01S 3/1608
  USPC .......................................................... 356/437
  See application file for complete search history.

(56) References Cited

U.S. PATENT DOCUMENTS

| | | | |
|---|---|---|---|
| 2011/0274386 A1 | 11/2011 | Bosselmann et al. | |
| 2019/0317130 A1* | 10/2019 | Sun ................... | G01D 5/35345 |
| 2020/0240820 A1* | 7/2020 | Boerhout ........... | G01N 21/3504 |

FOREIGN PATENT DOCUMENTS

| | | | |
|---|---|---|---|
| DE | 102012217479 B3 * | 10/2013 | ......... G01N 21/1702 |
| JP | 2002147059 A * | 5/2002 | |
| WO | WO-2015137999 A1 * | 9/2015 | ............. A61B 5/202 |

OTHER PUBLICATIONS

Ming Han, Tongqing Liu, Lingling Hu, and Qi Zhang, "Intensity-demodulated fiber-ring laser sensor system for acoustic emission detection," Opt. Express 21, 29269-29276 (2013).

Mejia Quintero, S.M.; Guedes Valente, L.C.; De Paula Gomes, M.S.; Gomes da Silva, H.; Caroli de Souza, B.; Morikawa, S.R.K. All-Fiber CO2 Sensor Using Hollow Core PCF Operating in the 2 µm Region. Sensors 2018, 18, 4393.

Y. Ran et al., "Vibration Fiber Sensors Based on SM-NC-SM Fiber Structure," in IEEE Photonics Journal, vol. 7, No. 2, pp. 1-7, Apr. 2015.

Scott N. Zhang, Dorothy Y. Wang, Jianmin Gong, Dian Fan, Bo Dong, Michael Fraser, Anbo Wang, "High-sensitivity electro-optic CO2 gas sensing based on absorption spectroscopy," Proc. SPIE 8376, Photonic Microdevices/Microstructures for Sensing IV (May 19, 2012).

Yanping Xu, Ping Lu, Zengguang Qin, Jeremie Harris, Farhana Baset, Ping Lu, Vedula Ravi Bhardwaj, and Xiaoyi Bao, "Vibration sensing using a tapered bend-insensitive fiber based Mach-Zehnder interferometer," Opt. Express 21, 3031-3042 (2013).

Xie W-G, Zhang Y-N, Wang P-Z, Wang J-Z. Optical Fiber Sensors Based on Fiber Ring Laser Demodulation Technology. Sensors. 2018; 18(2):505.

* cited by examiner

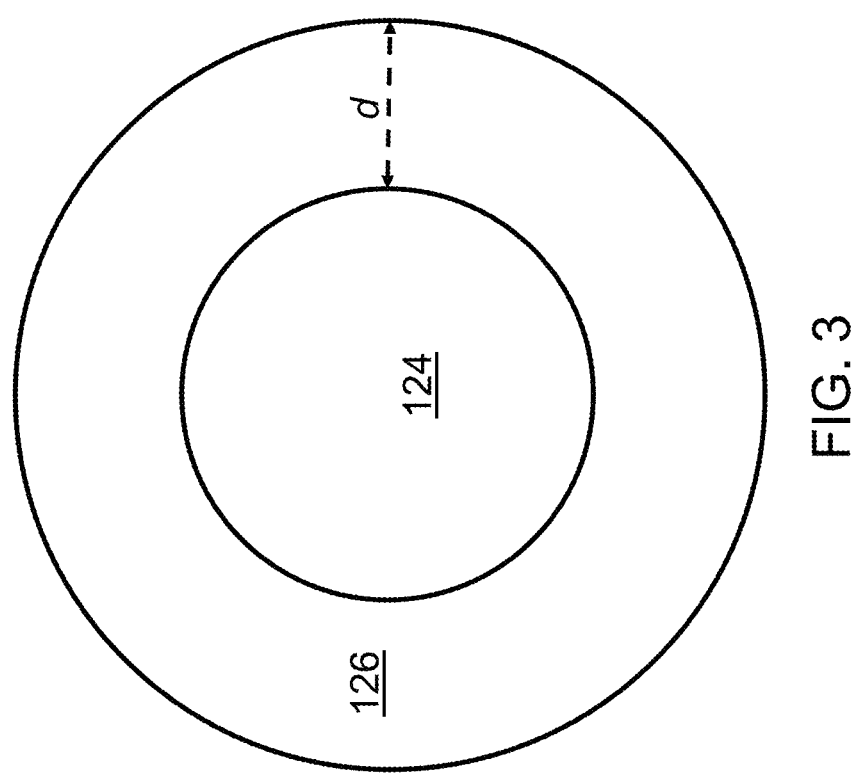

SIMULTANEOUS ULTRASONIC VIBRATION AND GAS SENSING BASED ON A TUNABLE FIBER RING LASER

CROSS-REFERENCE TO RELATED APPLICATIONS

This Utility Patent Applications claims priority benefit as a U.S. Non-Provisional of U.S. Provisional Patent Application Ser. No. 63/257,488, filed on Oct. 19, 2021, the entirety of which is incorporated by reference herein.

STATEMENT OF GOVERNMENT SUPPORT

The United States Government has rights in this invention pursuant to the employer-employee relationship of the Government to the inventors as U.S. Department of Energy employees and site-support contractors at the National Energy Technology Laboratory.

FIELD OF THE INVENTION

Embodiments relate to combination gas, vibration sensors suitable for use in a gas pipeline. More specifically, this invention relates to a sensor utilizing a tunable fiber ring laser suitable for simultaneous monitoring for the presence of a gas and for vibration in the environment of the sensor.

BACKGROUND

Natural gas is a critical commodity in the U.S. and other countries, provided and transported through sprawling infrastructure. As natural gas is such an important commodity, it is necessary to monitor the health, ideally in real time, of the infrastructure used in the natural gas ecosystem. Vibration and gas monitoring are important components of real-time structural health monitoring of said infrastructure. Monitoring and quantifying the vibration levels in pipelines and in other critical infrastructure are essential for early damage detection, structural safety, and maintenance scheduling. Gas sensors can provide gas leak warning outside the pipe or monitor gas composition inside the pipeline. For example, $CH_4$ gas monitoring can inform gas leaks of a natural gas pipeline; $CO_2$ monitoring can inform gas leaks of a $CO_2$ transportation pipeline, and water vapor monitoring can indicate corrosivity inside the gas pipelines.

Conventional vibration sensors have tremendous disadvantages. Many state of the art vibration sensors use piezoelectric materials. Sensors based on piezoelectric materials are incompatible with harsh environmental conditions and suffer from electromagnetic interference.

Fiber optic sensors are suitable for use in the monitoring of gas infrastructure. Fiber optic sensors advantageously exhibit high sensitivity, immunity to electromagnetic interference, low weight, easy installation, corrosion resistance, harsh environmental capabilities, and improved safety in flammable gases compared to electrical-based sensors.

While fiber optic sensors offer these advantages, current state of the art fiber optic sensor systems also have disadvantages. State of the art fiber optic vibration sensors include fiber Bragg gratings (FBG) or Sagnac and Mach-Zehnder interferometers (MZI). Fabrication and processing of these state of the art sensors are difficult. Further, these state of the art sensors suffer from low sensitivity. Current fiber optic vibration sensors rely on the demodulation of external vibration induced peak wavelength shift which requires a relatively long measurement time to obtain a steady state spectrum. Such spectral shift detection with a slow response time is not suitable for sensing rapidly and dynamically changing environments.

Moreover, in the state of the art, monitoring two different kinds of parameters (vibration and gas) requires two diverse sensor systems with an expensive laser source and other costly components, which makes a multi-parameter sensor system more complex and unaffordable. The present invention overcomes these problems using a single fiber optic sensor interrogator that can measure dynamic vibrations and gas concentration at the same time, both measurements made using low-cost components.

A need in the art exists for a cheap and reliable sensor suitable for simultaneously sensing vibration and the presence of a target gas.

SUMMARY

One object of the invention is providing a sensor suitable for simultaneous monitoring of vibration and the presence of gas species of interest in gas infrastructure (natural gas or other gasses). The invented sensor comprises a tunable fiber ring laser cavity, means for measuring vibration, and means for measuring the presence of a gas of interest. Said sensor is suitable for deployment on or near infrastructure used in transporting, holding, or processing gasses.

The invented gas and vibration sensor have demonstrated superior suitability for continuous, in-situ use. Said sensor is suitable for placement in a location for sensing remote from a user reading data obtained from said sensor.

The invented tunable fiber ring sensor for simultaneous sensing of vibration and the presence of a target gas provides the first demonstration of simultaneous monitoring of vibration and gas (or two parameters simultaneously at all) using a fiber ring laser and has many applications. For the application of pipeline monitoring, two-parameter simultaneous sensing can enhance measurement accuracy and ensure the detection of predictive signs or early gas leaks. For example, abnormal vibration or acoustic signals can indicate defects or erroneous operation of the pipeline before gas leaks. The gas monitoring provides alerts for direct gas leak detection. For the $CO_2$ monitoring as an example, it can be used for $CO_2$ pipeline leak detection, and it's also relevant for $CO_2$ caused corrosion of steel pipes as the impurity of $CO_2$ dissolved in water generates corrosive environments. Moreover, the proposed invention is attractive for emerging applications, where simultaneous measurement of $CO_2$ and vibrations are needed, for instance, gas turbines, aviation fuel tanks, etc. This multivariant analysis provides a more thorough understanding of the state of pipeline condition than a single parameter measurement. The answer provided is more state-specific—in other words, is the pipeline experiencing repetitive strain, is it close to a failure mode, or is it leaking already.

Briefly, the invention provides a system for simultaneously detecting vibration and the presence of a target gas comprising: a tunable fiber ring laser in electronic and optical communication with a vibration sensor and a gas detection sensor.

The invention also provides a method for simultaneously measuring vibration and detecting the presence of a target gas in an environment comprising: providing a system for simultaneously measuring vibration and detecting a target gas into an environment; sending an optical signal to a vibration sensor and gas detection sensor; and collecting and analyzing modified signals from the vibration sensor and gas detection sensor.

BRIEF DESCRIPTION OF THE DRAWINGS

The invention together with the above and other objects and advantages will be best understood from the following detailed description of the preferred embodiment of the invention shown in the accompanying drawings, wherein:

FIG. 3 is a cross-section of an embodiment of a gas sensor used in the present invention, in accordance with the features of the present invention;

DETAILED DESCRIPTION

The foregoing summary, as well as the following detailed description of certain embodiments of the present invention, will be better understood when read in conjunction with the appended drawings.

The following detailed description should be read with reference to the drawings in which similar elements in different drawings are numbered the same. The drawings, which are not necessarily to scale, depict illustrative embodiments and are not intended to limit the scope of the invention.

In an embodiment, the present invention provides, a simple and low-cost sensor capable of simultaneous vibration and gas sensing (detection of the presence of a gaseous moiety), said sensor using a single, tunable fiber ring laser. Surprisingly and unexpectedly, the inventors have discovered a sensor using a tunable fiber ring laser that can simultaneously detect vibration and the presence of a target gas. The invented sensor provides the first demonstrated simultaneous vibration and gas monitoring with a simple, and low-cost fiber interrogator. In an embodiment, the sensor that is highly sensitive to vibration is based on a single-mode—multimode—single-mode (SMS) fiber structure, said sensor comprising a laser ring cavity, which significantly enhances the signal-to-noise ratio and narrows the spectral bandwidth compared to prior art sensors.

The figures depicting the instant invention may feature abbreviations indicating the identity of particular components. For example, in the figures, PC is an abbreviation for polarization controller, ISO is an abbreviation for isolator, WDM is an abbreviation for wavelength division multiplexer, MMF is an abbreviation for multimode fiber, PD is an abbreviation for photodetector, TEOS is an abbreviation for tetraethoxysilane, RF is an abbreviation for radio frequency, Comp is an abbreviation for a computer and or detector, and PZT is an abbreviation for piezoelectric transducer.

Figure 1A:
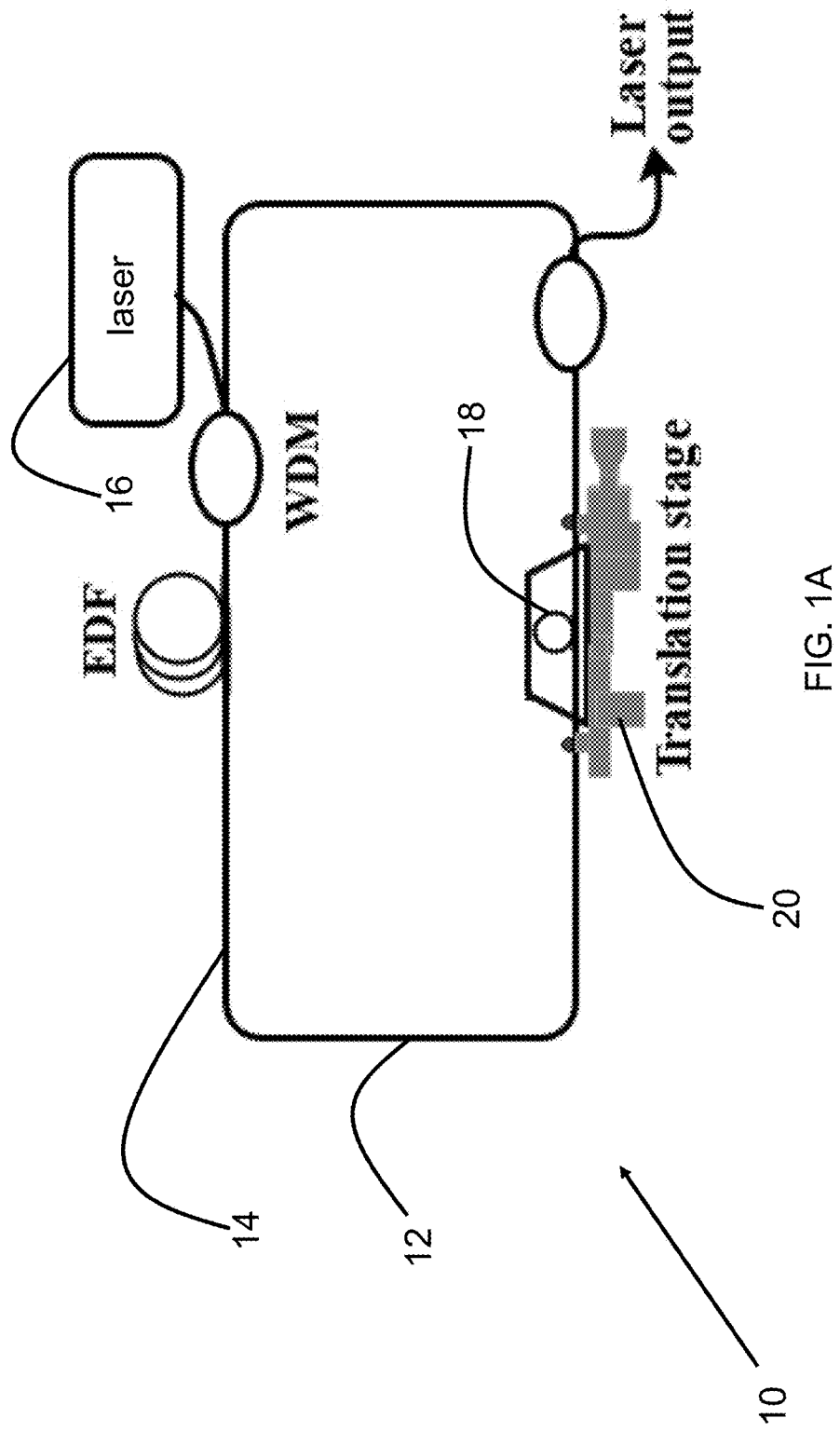
FIG. 1A is a simplified schematic of a tunable fiber ring laser, in accordance with the features of the present invention.
Figure 1B:
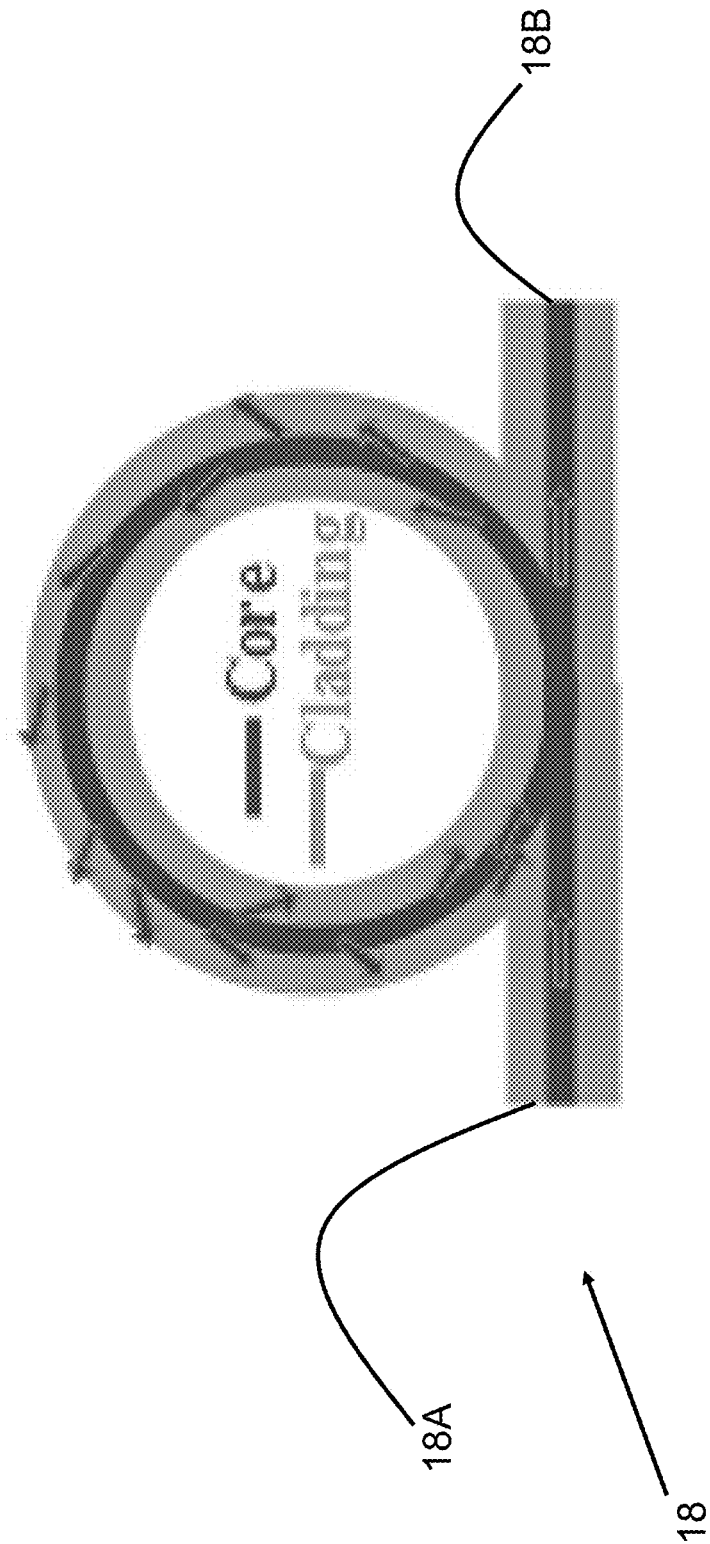
FIG. 1B is a detail view of a secondary fiber loop of a tunable fiber ring laser, in accordance with the features of the present invention.

FIG. 1A depicts a simplified schematic of a tunable fiber ring laser cavity 10. The fiber ring laser cavity 10 comprises a loop 12 of fiber 14 placing a laser 16 in optical communication with a secondary loop 18. Said secondary loop 18 is a small loop of fiber 14 positioned along the length of the fiber 14 making up the loop 12 of the fiber ring laser. As shown in FIG. 1A, the secondary loop 18 is positioned on a translation stage 20. The first end 18A of the secondary loop 18 (shown in FIG. 1B) is fixed in place with the second end 18B of the secondary loop 18 (shown in FIG. 1B) positioned on the translation stage 20 so that said second end 18B of the secondary loop 18 moves with movement of the translation stage 20.

In an embodiment, the laser 16 is any laser suitable to send a light signal through the fiber 14 comprising the cavity 10. Suitable lasers include wavelength pump lasers. As described herein, the wavelength emitted by the fiber ring laser 10 can be modified from the wavelength of the initial signal emitted by the laser 16. In an exemplary embodiment, the pump laser is a 980 nm or 1480 nm pump laser.

In an embodiment, the fiber 14 is any fiber suitable for carrying the optical signal from the laser 16. In the embodiments described herein and shown in the accompanying figures, the fiber 14 comprises single-mode fiber. The single-mode fiber may comprise erbium-doped fiber. In other embodiments, the fiber 14 comprises multimode fiber, large-mode-area fiber, single-mode fiber, and combinations thereof.

Figure 2A:
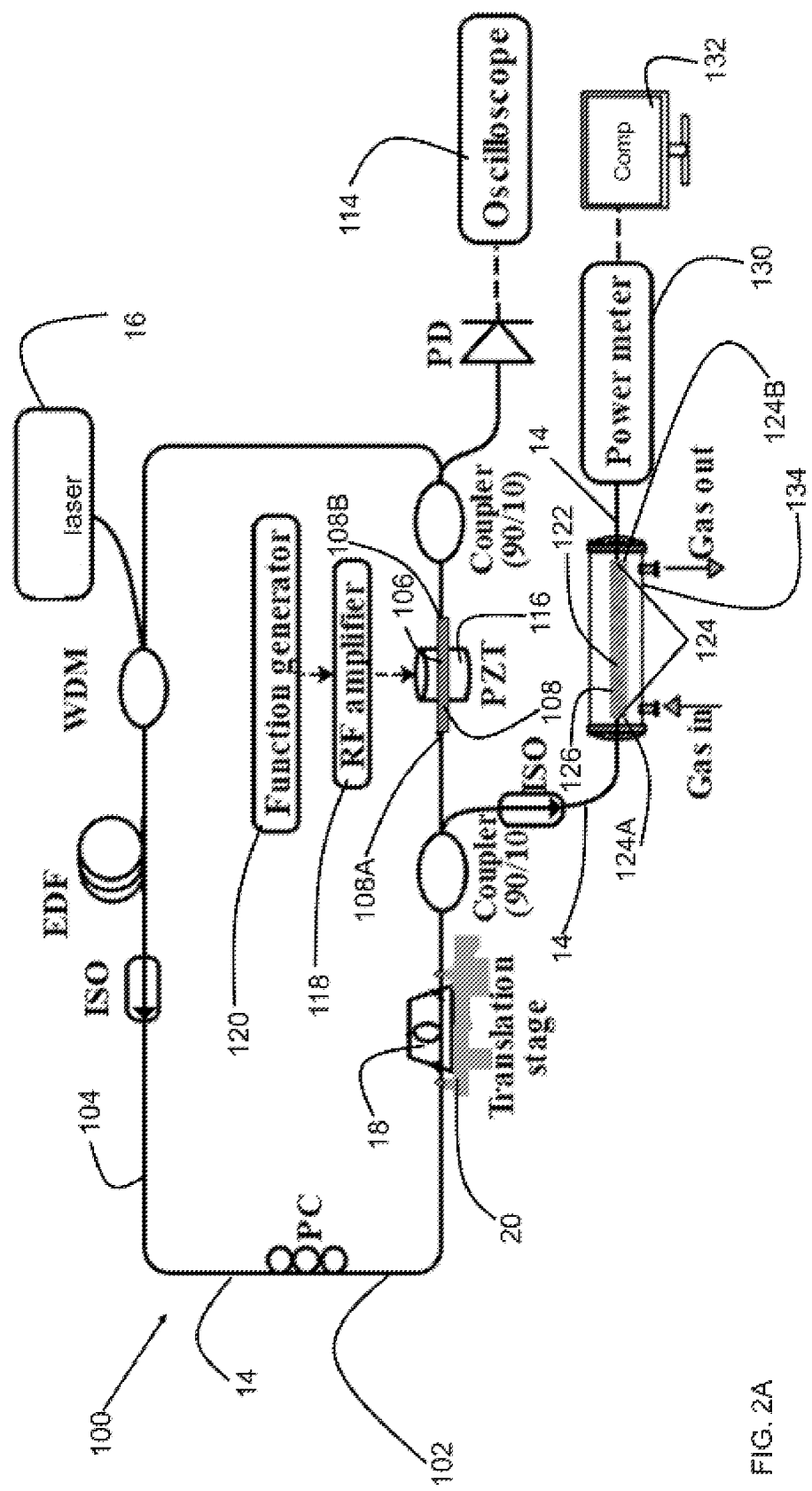
FIG. 2A is a simplified schematic of a system for simultaneously measuring vibration and detecting the presence of a target gas using a tunable fiber ring laser to interrogate vibration and gas detection sensors.

FIG. 2A shows a simplified schematic of a system 100 for simultaneously measuring two parameters using a tunable fiber ring laser 102. As shown in FIG. 2A, the system 100 comprises a fiber ring laser 102 comprising a loop 104 of fiber 14 placing a laser 16 in optical communication with a secondary loop 18. Said secondary loop 18 is a small loop of fiber 14 positioned along the length of the fiber 14 making up the fiber ring laser cavity 102. As shown in FIG. 1A, the secondary loop 18 is positioned on a translation stage 20. The first end 18A of the secondary loop 18 (shown in FIG. 1B) is fixed in place with the second end 18B of the secondary loop 18 (shown in FIG. 1B) positioned on the translation stage 20 so that said second end 18B of the secondary loop 18 moves with movement of the translation stage 20.

A salient feature of the invention is the ability to tune the wavelength output of the fiber ring laser shown in FIGS. 1A, 2A, 4, and 5. In an embodiment, the wavelength output of the fiber ring laser is tuned or adjusted by changing the diameter or placing strain on the fiber 14 comprising the secondary loop 18. Placing strain on the fiber 14 comprises fixing the location of the first end 18A (shown in FIG. 1B) of the secondary loop 18 and moving the second end 18B (shown in FIG. 1B) of the secondary loop 18 with the translation stage 20.

Fixing the first end 18A of the secondary loop 18 while moving the second end 18B the translation stage 20 will cause the diameter of the secondary loop 18 to change. Therefore, the resonance peak wavelength of the ring laser 10, 102 changes linearly with the applied displacements of the secondary loop 18 with a sensitivity of 227.5 pm/mm. The relationship between the laser rings resonance peak wavelength and secondary loop radius of curvature is described in Equation 1 below where A is the resonance peak wavelength of the laser 10, 102 R is the curvature radius of the secondary loop 18, and x is the distance from the fiber cross-section center.

$$\frac{d\lambda}{dR} = \frac{\lambda}{R+x} \qquad \text{Equation 1}$$

Looking to Equation 1, changing the curvature radius of the secondary loop 18 by displacing the second end 18B of said secondary loop changes the wavelength of the ring laser 10, 102 output spectrum. Since the lasing wavelength depends on the secondary loop 18 curvature radius, the secondary loop radius can be fixed using the translation stage to result in a desired output wavelength from the ring laser 10, 102. In an exemplary embodiment, the wavelength of the ring laser 10, 102 is adjusted to correspond with the absorption wavelength of a gas to be detected using the instant invention. As such, the ring fiber laser discussed herein is tunable and is configured such that the ring fiber laser can be adjusted to output a desired wavelength. An exemplary wavelength is approximately 1574.6 nm, the absorption wavelength of $CO_2$.

A salient feature of the invention is the use of a fiber ring laser as a single interrogator based on a fiber ring laser for simultaneous interrogation of a vibration and gas detection sensor. Prior art systems would require more than one type of interrogator to interrogate vibration and gas detection sensors.

Figure 4:
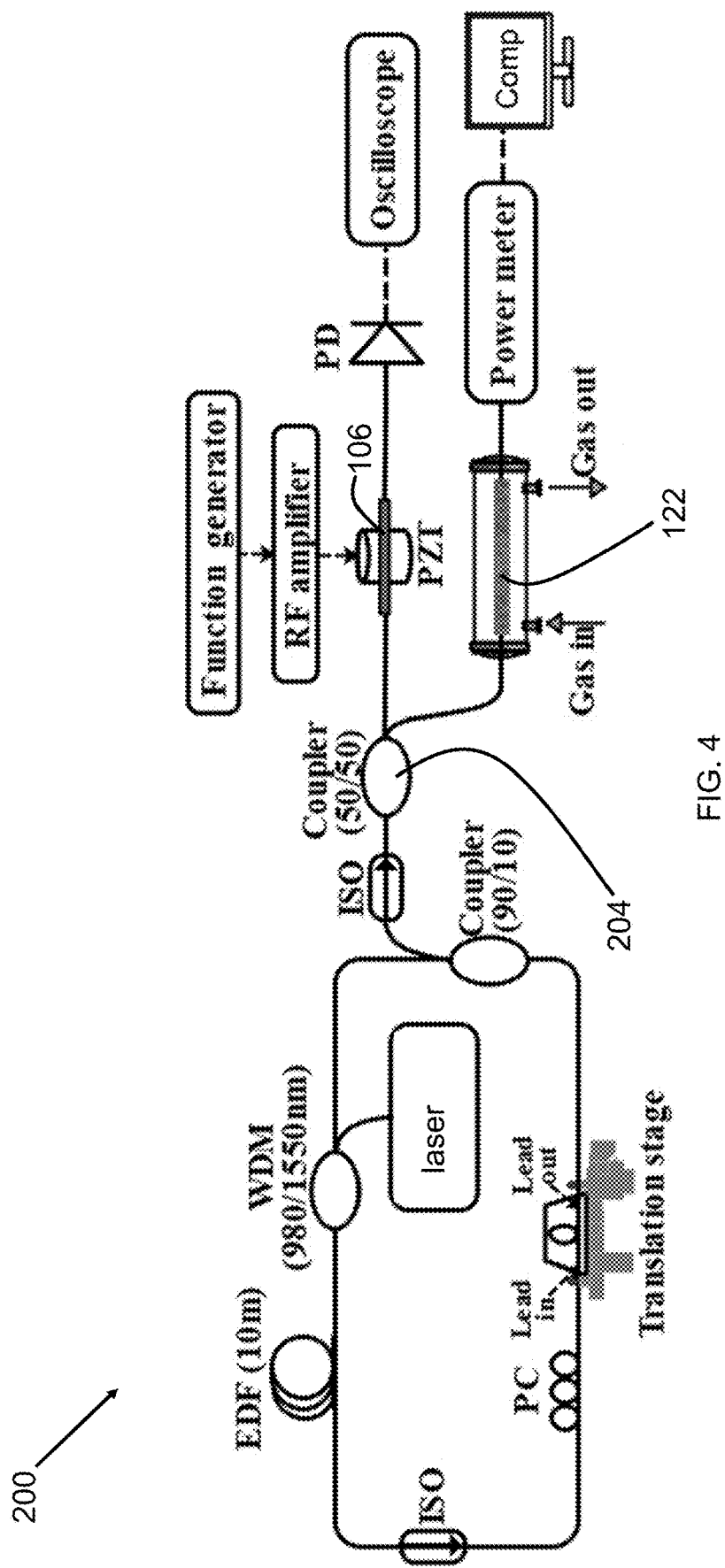
FIG. 4 is a simplified schematic of an alternative system for simultaneously measuring vibration and detecting the presence of a target gas using a tunable fiber ring laser to interrogate vibration and gas detection sensors, in accordance with the features of the present invention.
Figure 5:
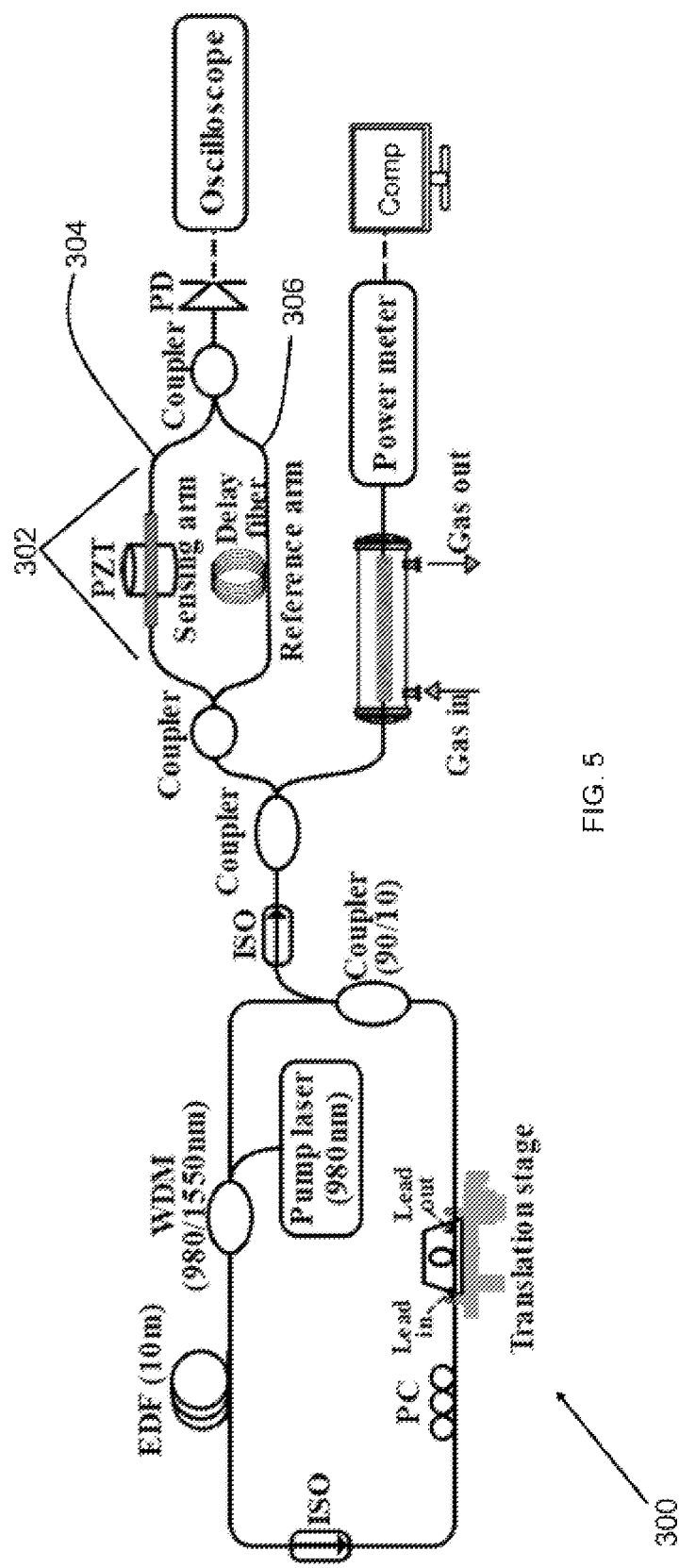
FIG. 5 is a simplified schematic of an alternative system for simultaneously measuring vibration and detecting the presence of a target gas using a tunable fiber ring laser to interrogate vibration and gas detection sensors, in accordance with the features of the present invention.

Another salient feature of the invention is its robustness. The invented systems of FIGS. 2A, 4, and 5 are suitable for deployment within harsh environments such as near gas compressor stations along pipelines, or in super-critical $CO_2$ power plants, Further, the systems are suitable for continuous and in-situ operation, meaning continuous and in-situ and simultaneous monitoring of vibration and gas detection within the deployment environment.

The system 100 shown in FIG. 2A comprises a system for simultaneously monitoring vibration and detecting the presence of a target gas or gaseous moiety. Looking to FIG. 2A, a vibration sensor 106 is coupled to and in optical and electronic communication with the fiber ring laser. The vibration sensor 106 comprises a length of multimode fiber 108 extending between first 108A and second ends 108B. Said multimode fiber 108 is spliced to single-mode fiber 14 at both ends such that length of multimode fiber 108 extends between, is sandwiched between, single-mode fiber 14; wherein said multimode fiber is in electronic and optical communication with said single-mode fiber. As shown in FIG. 2A, the system 100 features the vibration sensor 106 positioned within the cavity of the fiber ring laser 102, i.e. positioned within the loop 104 along the length of fiber 14.

Figure 2B:
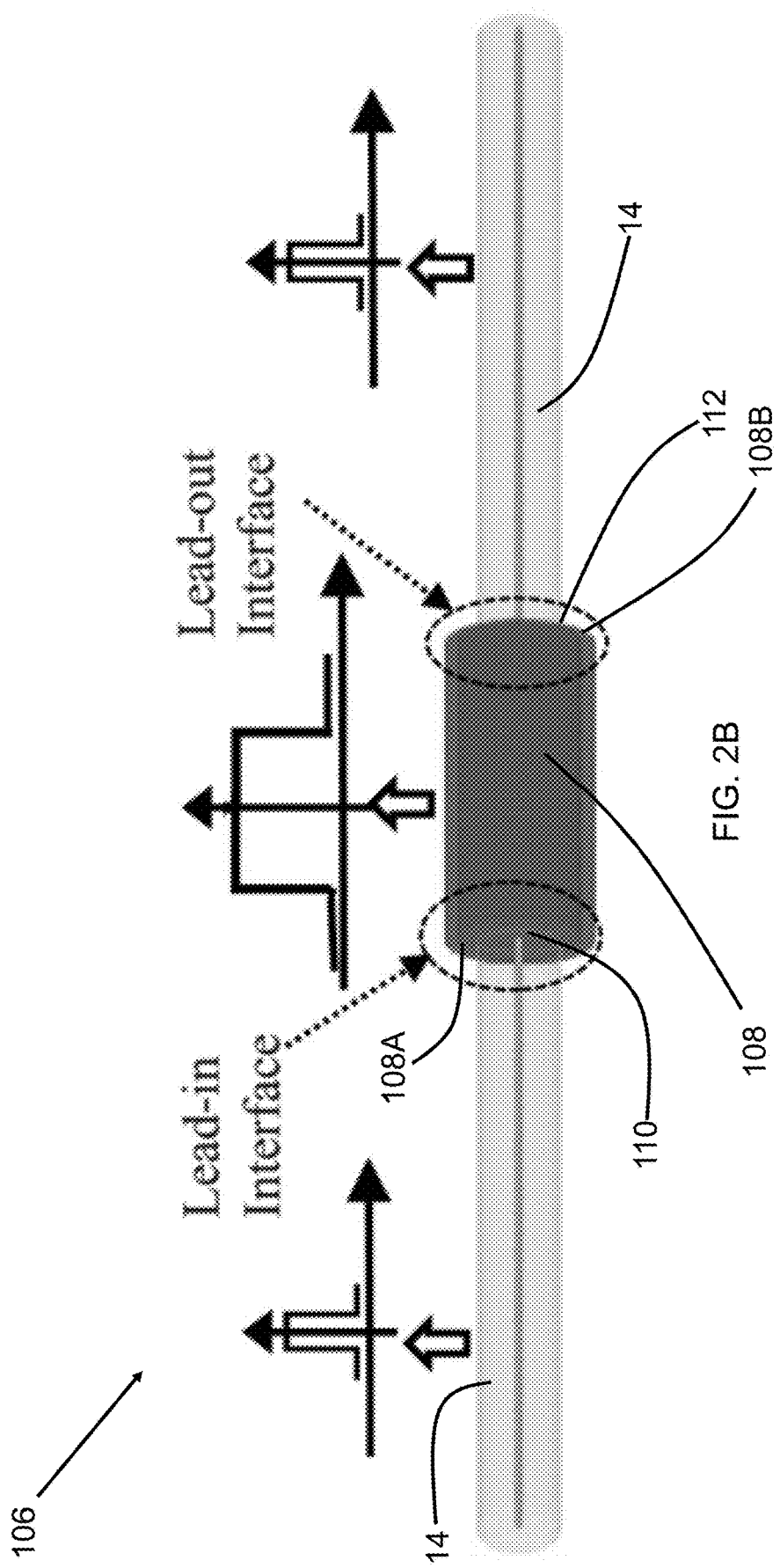
FIG. 2B is a detail view of an embodiment of a vibration sensor used in the present invention, in accordance with the features of the present invention.

FIG. 2B is a detail view of the vibration sensor 106. The vibration sensor 106 comprises a first interface 110 (lead-in interface), the interface between the single-mode fiber 14 and the first end of the multimode fiber 108A. The vibration sensor 108 also comprises a second interface 112 (lead-out interface), the interface between the second end of the multimode fiber 108B and the single-mode fiber 14. In operation, light is injected into the multimode fiber section 108 through the first (lead-in) interface 110, exciting multiple modes that propagate with interference along the length of the multimode fiber 108 section with their corresponding propagation constants. At the second interface (lead-out) interface 112, the multiple modes generated in the multimode fiber 108 couple into single-mode fiber 14 contacting the second end of the multimode fiber 108B.

In practice, the output power at the second interface 112 is determined by the mode interference between the various modes in the multifiber fiber 108 and the coupling between the second end of the multimode fiber 108B and the single-mode fiber 14, which is significantly dependent on the physical properties of the multimode fiber 108 section. When the multimode fiber 108 experiences an external vibration, the fiber undergoes a tensile and compressive strain. As a result, when the multimode fiber 108 is receiving an optical signal and is subject to (receives) vibration, the transmission spectrum emanating from said multimode fiber 108 will periodically blue-shift or red-shift. Therefore, at a certain vibration frequency, the resultant spectrum intensity increases and decreases. An oscilloscope or other device 114 suitable for measuring vibration in optical and electronic communication with and downstream from said vibration sensor 106 is used to collect and provide vibration data from said vibration sensor 106.

FIG. 2A depicts a version of the system 100 used for testing purposes. For testing purposes, the system 100 includes a piezoelectric transducer (PZT) 116 in contact with the multimode fiber 108 of the vibration sensor 106. In the testing configuration shown in FIG. 2A, said PZT 116 is in electronic communication with an RF amplifier 118 and function generator 120. The PZT 116, RF amplifier 118, and function generator 120, are components used to generate test vibration spectra wherein the function generator and RF amplifier cause the PZT to vibrate, generating a vibration spectra from the vibration sensor 106. In embodiments of the system deployed to detect vibration occurring in the sensor's surroundings, the PZT 116, RF amplifier 118, and function generator 120 are omitted from the system.

As described above, FIG. 2A shows a system 100 for simultaneous monitoring of vibration and detecting the presence of a target gas. As such, the system 100 comprises a gas detecting sensor 122 coupled to and in electronic and optical communication with the fiber ring laser 102. As shown in FIG. 2A, the gas detecting sensor 122 comprises a length of coreless fiber 124 extending between first 124A and second ends 124B. Said coreless fiber 124 is spliced to single-mode fiber 14 at both ends such that length of coreless fiber 124 extends between, is sandwiched between, single-mode fiber 14. The coreless fiber 124 is coated with a gas sensing material 126 such that said gas sensing material 126 overlays and surrounds said coreless fiber 124. In an embodiment, the gas detecting sensor 122 is upstream from and in optical and electronic communication with a power meter 130 and detector 132, wherein the coated coreless fiber section 124, power meter 130, and detector 132 are all in optical and electronic communication.

FIG. 3 depicts a cross-section of the coreless fiber 124 of the gas detecting sensor 122 with the gas sensing material 126 surrounding the coreless fiber 124. The coating of gas sensing material 126 surrounding the coreless fiber 124 has a thickness d. In an embodiment, d is between 100 nm and 800 nm. The thickness of the gas sensing material layer 126 can be tuned to suit the system embodying the instant invention being deployed.

The gas detecting sensor 122 shown in FIGS. 2A, 4, 5, is in electronic and optical communication with a downstream computer or other detector 132 suitable for collecting and analyzing optical signal emanating from said gas detecting sensor 122.

A salient feature of the invention is the gas sensing material 126 used as an overlayment (coating) on the coreless fiber 124 portion of the gas detecting sensor 122. The gas sensing material 126 comprises any material that exhibits a measurable variation to an optical constant in response to the presence of gasses around or contacting said gas sensing material 126. In an embodiment, the gas sensing material 126 is selected from highly absorptive materials whose refractive index is close to underlying optical fiber. In those embodiments, the gas sensing response of the invented gas detecting sensor 122 is based on the infrared absorption of the absorbed gas in the sensing materials, such as porous TEOS. In other embodiments, the gas sensing material 126 is selected from absorptive materials whose overall refractive index will change when gas is absorbed in the sensing materials such as Metal-organic frameworks (MOFs), polymer based materials, nanomaterials, and combinations thereof. Preferable gas sensing materials 126 have high gas sorption capacity and good gas selectivity, good film formation capability, and good stability. The invented systems can be customized such that the gas sensing material 126 is selected for detecting a particular gas or combinations thereof.

In an embodiment, the gas sensing material is chosen for its suitability for detecting the presence of a particular gas. For example, tetraethoxysilane (TEOS) comprises an exemplary and suitable material gas sensing material for detecting the presence of $CO_2$.

In an embodiment, the gas sensing material 126 is applied to an underlying fiber using any suitable procedure for providing the gas sensing material onto the fiber. Exemplary procedures include sol-gel coating, atomic layer deposition, dip coating, sputtering deposition, and combinations thereof.

As described herein, the invented system is suitable for detecting vibration in the environment of the vibration sensor 106. As such, the systems 100, 200, 300 and associated vibration sensors are configured to detect vibration in the environment surrounding said vibration sensor. In an embodiment, the invented system is suitable for detecting vibration with a frequency between approximately 10 Hz and approximately 400 kHz.

The present disclosure describes using the invented systems 100, 200, 300 particularly the gas sensor 122, to detect the presence of a target gas, particularly $CO_2$. As such, the systems 100, 200, 300 and associated gas sensors 122 are configured to detect the presence of a target gas. $CO_2$ is an exemplary target gas and is not meant to be limiting. In an embodiment, the systems 100, 200, 300 and gas detecting sensors 122 can be customized to detect the presence of any gas or combinations thereof. Additional and exemplary target gasses detectable by the invented system 100 include $CO_2$, CO, $CH_4$, $H_2$, water vapor, natural gas, syngas, and combinations thereof. The invented system and associated gas sensor are suitable for detection of a target gas in miniscule concentrations. In an embodiment, the invented system is suitable for detecting a target gas present in concentrations between approximately 0.5% by volume and approximately 100% by volume in the environ surrounding the gas sensor 122 of the system.

Returning to FIG. 2A, the system 100 depicted therein features a housing 134 surrounding the coated coreless fiber portion 124 of the gas sensor 122, wherein said housing 134 comprises a gas inlet and outlet. The housing 134 depicted in FIG. 2A is an optional feature used to direct a particular gas or a particular gaseous flow onto the coated coreless fiber portion 124. When the invented systems 100, 200, 300 are deployed, the housing 134 can either be omitted from the system or a particular gaseous flow can be directed into the housing.

FIG. 4 is a simplified schematic for an alternative embodiment of a system 200 for simultaneous vibration and gas detection. This embodiment 200 removes the vibration sensor 106 from the laser ring cavity as it is positioned as shown in FIG. 2A and splits the tuned fiber ring laser into two paths using a 50/50 fiber coupler 204, one path for the vibration sensor 106 and one for the gas detection sensor 122. As with the system 100 shown in FIG. 2A, the PZT, function generator, RF amplifier, and housing 134 are optional features that need not be included upon deployment in a testing environ.

FIG. 5 is a simplified schematic for yet another embodiment of a system 300 for simultaneous vibration and gas detection. This embodiment 300 uses a Mach-Zehnder interference structure 302 as a vibration sensor. In the embodiment 300 shown in FIG. 5, signal from the ring laser to the vibration sensor 302 is split into two arms, namely the sensing arm 304 and the reference arm 306. The sensing arm 304 is modulated by the vibrations and interferes with the reference signal using another fiber coupler. The vibration signal is acquired by the phase difference between the sensing arm and the reference arm.

A salient feature of the invention is that the described systems for sensing vibration and detecting the presence of a target gas are configured for detecting both vibration and the detecting the presence of a target gas simultaneously. Prior art systems require separate vibration and gas detection modalities.

Figure 6:
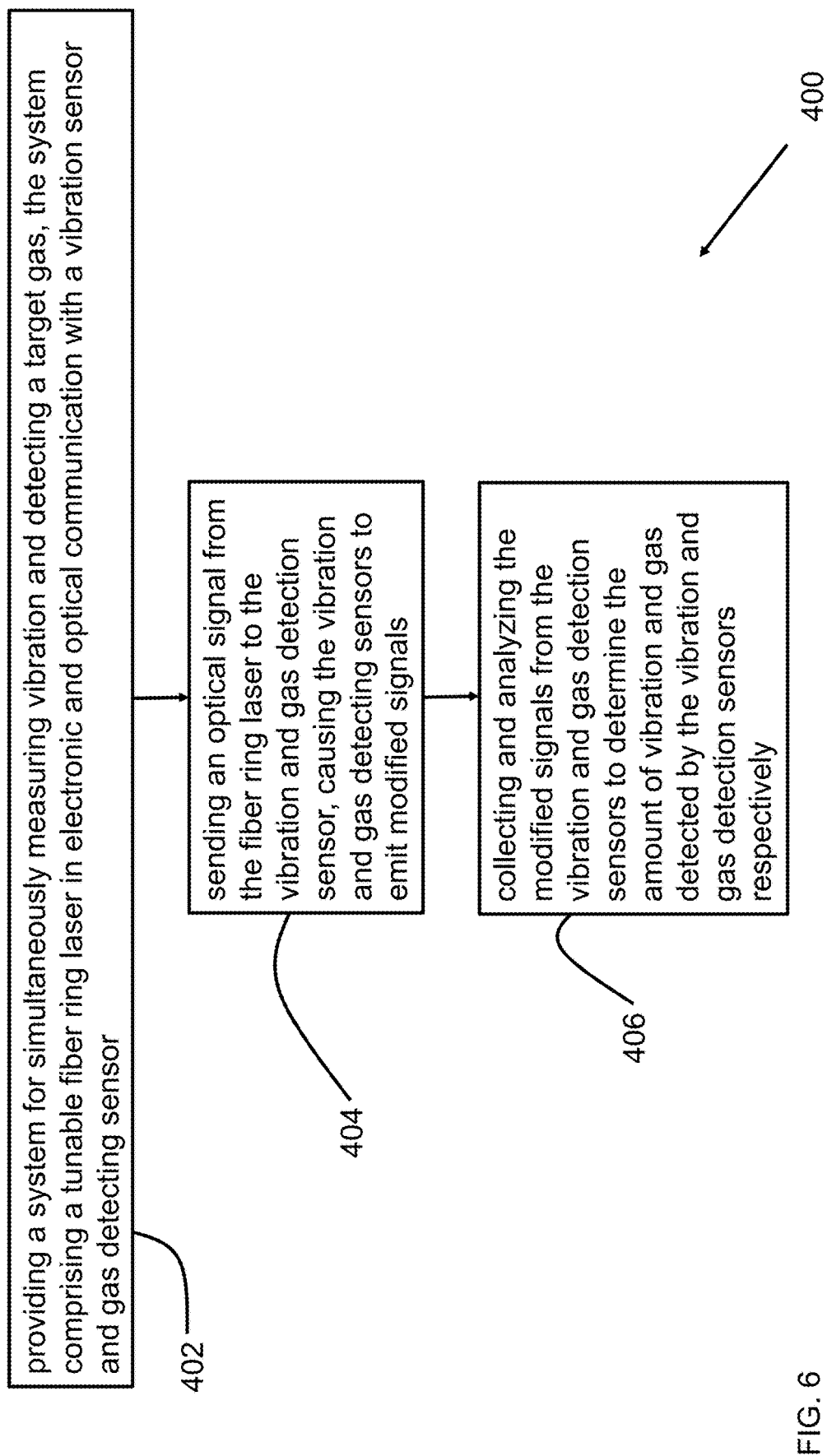
FIG. 6 is a flow chart for a method for simultaneously measuring vibration and detecting a target gas, in accordance with the features of the present invention.

FIG. 6 depicts a flow chart for a method 400 for simultaneously measuring vibration and detecting a target gas. The method 400 begins by providing a system for simultaneously measuring vibration and detecting a target gas 402, wherein the system is a tunable fiber ring laser in electronic and optical communication with both a vibration sensor and a gas detection sensor. The method continues with sending an optical signal from the fiber ring laser to the vibration and gas detection sensor 404, causing the vibration sensor to emit a modified signal that differs from the original signal from the tunable fiber ring laser based on the amount of vibration that is incident upon the vibration censor, and causing the gas detection sensor to emit a modified signal that differs from the original signal from the tunable fiber ring laser based on the amount of a target gas present around the gas detection sensor. The method continues by collecting and analyzing the modified signals from the vibration and gas detection sensors to determine the amount of vibration and gas detected by the vibration and gas detection sensors respectively 406. The method 400 simultaneously provides signals from the tunable fiber ring laser to the vibration and gas detection sensors and also simultaneously generates vibration and gas detection data.

Surprisingly and unexpectedly, the invented systems and methods described herein provide simultaneous gas and vibration detection using a single fiber ring laser based interrogator. The invented systems and methods provide simultaneous, continuous, and in-situ sensing capabilities for gas and vibration sensing. In existing equipment, these two parameters are measured with two completely disparate and expensive pieces of equipment. This makes utilization of both parameters for $CO_2$ pipeline integrity monitoring significantly more challenging and expensive. In the system proffered by the instant invention, the cost of measuring both parameters is reduced via specific choices in component selection and operating wavelength such that both can be measured readily with the same optical fiber configuration. While the need for such capabilities is increasing via technological advances in both carbon sequestration, which requires transport of large volumes of $CO_2$; and supercritical $CO_2$ power plants, which rely on high pressure $CO_2$ plumbing to increase operating efficiency, this is the only known instrumentation design to purport low-cost fiber-optic measurement of both $CO_2$ content and vibration for the safe monitoring of these advanced energy systems. The system can be deployed for monitoring these piping systems, in order to detect flaws and leaks in the system more rapidly during operation. Moreover, the system and methods described herein are suitable for detecting gasses other than and in combination with $CO_2$, making the invention suitable for use in the economies and environs containing other gasses of interest such as CO, $CH_4$, $H_2$, water vapor, natural gas, syngas, and combinations thereof.

In an exemplary embodiment of the fiber ring laser 10, 102 the fiber ring laser is comprised of a few meters of erbium-doped fiber (EDF), a 1550/980 nm wavelength division multiplexer (WDM), and a 980 nm pump laser. When the EDF is pumped by a 980 nm laser, stimulated emission will arise. A 10 m EDF fiber acts as an active gain medium, which is pumped by a 980 nm laser diode through a 1550/980 nm WDM coupler. In another embodiment, thereafter, the stimulated signal passes through an isolator and polarization controller (PC). The isolator is employed to make sure the lasing only follows one direction around the fiber loop. The PC is used to counteract the polarization-dependent losses from components in the laser cavity. A 90/10 coupler can be used to tap out the lasing wavelength for detection.

Particular wavelengths of light are shown and described as used by the sensors shown in FIGS. 2A, 4, and 5. These wavelengths are exemplary and not meant to be limiting. A salient feature of the invention is the tunability of the fiber ring laser. As such, a user may select the wavelength(s) of light used in one of the invented sensors to correspond with detection of a desired gas species or a plurality of gas species.

In an embodiment, the invented sensors are suitable for placement on or near gas infrastructure where a user can monitor the sensor data remotely, allowing for use of the invented sensors in harsh environs not suitable for constant occupation by human users.

The invention is suitable for use in a wide variety of applications where vibrations and gas monitoring are important for infrastructure heath monitoring. The invention can be used to sense dynamic vibrations for critical infrastructure and monitoring gas concentrations (e.g. $CO_2$ and other gasses), including the following applications: oil/gas pipelines, wellbore integrity, $CO_2$ transportation pipelines, nuclear reactors, gas turbines, transportation, $CO_2$ sequestration and separation equipment, aeronautics, compressed gas processing, dry-ice manufacturing, and combinations thereof.

The invention may also be utilized for real-time production flow monitoring, power plants, heating, ventilation and air conditioning (HVAC) and healthcare. These sensing systems are applicable to monitor across a wide variety of industries. Furthermore, this invention can also be used to quantify the dynamic strain variations using the vibration sensor.

Numerous installation configurations are envisioned for the invented sensors, with applications inside pipelines or outside. For leak detection, the sensors can be installed outside the pipe, although for mixed-gas quantification could utilize the sensors inside the pipe. The vibration sensing is invariant to location and could be installed inside, outside, or in both locations along a pipe. The fiber ring laser-based sensor can be placed in high-risk locations along the pipeline (internal and/or external) to inform early risks. For other applications, this sensor also has the advantage of accessing limited space due to the small size and flexibility of optical fibers. In some embodiments, the fiber ring laser and associated vibration sensor are deployed on the outside of a pipeline with only the coated fiber portion of the gas sensor deployed inside the pipeline.

A salient feature of the invention is the use of a tunable fiber ring laser to simultaneously measure two parameters. In alternative embodiments, one or more additional sensors can be added to the designs shown and described herein so that three or more parameters can be measured using one tunable fiber ring laser.

Ring Fiber Laser Tuning Detail

Figure 7A:
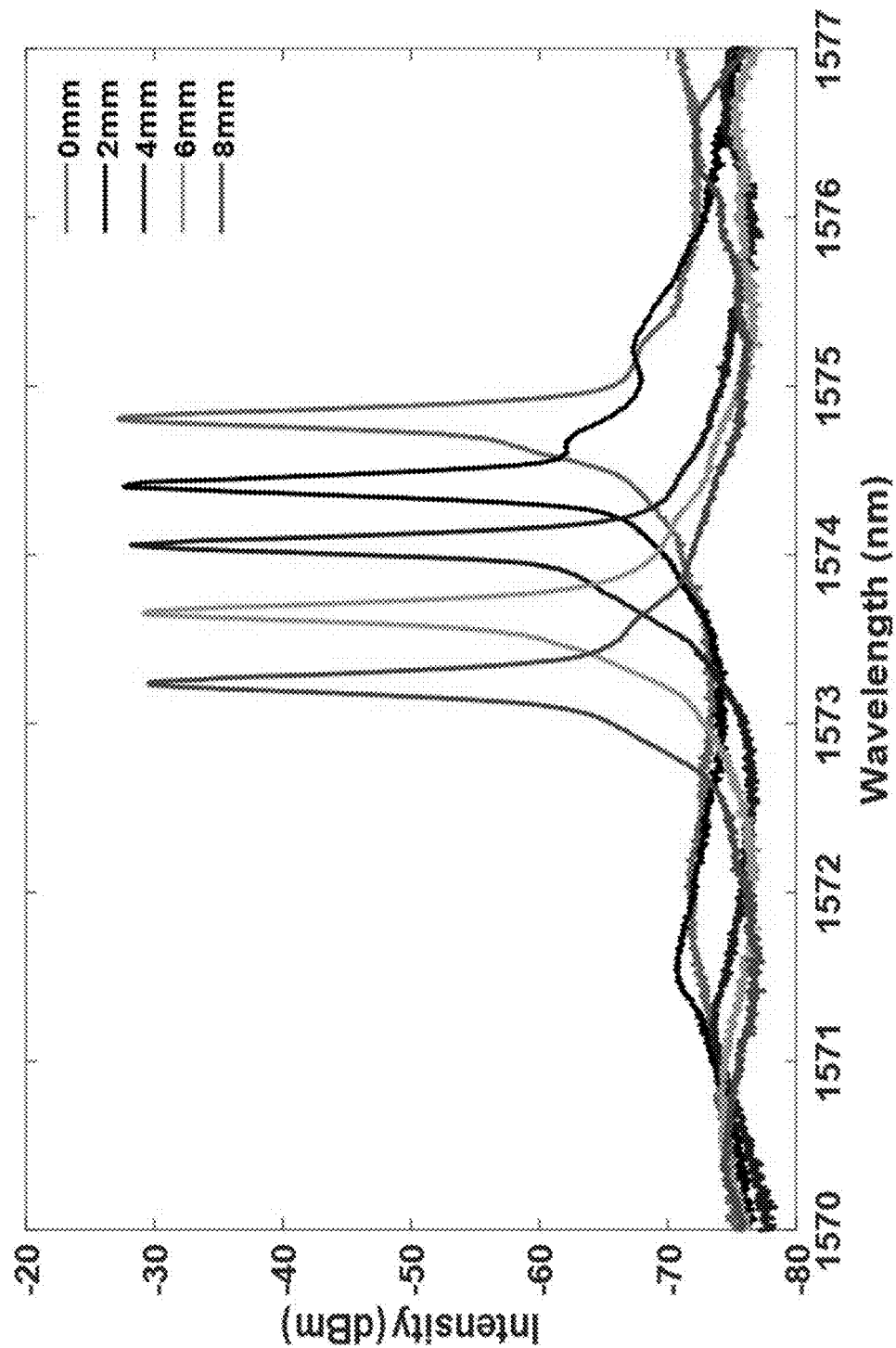
FIG. 7A is a graph of light intensity vs. wavelength obtained by displacing the secondary fiber ring portion of an embodiment of the fiber ring laser used in the present invention shown in FIGS. 1A, 2A, 4, and 5 various distances, in accordance with the features of the present invention.
Figure 7B:
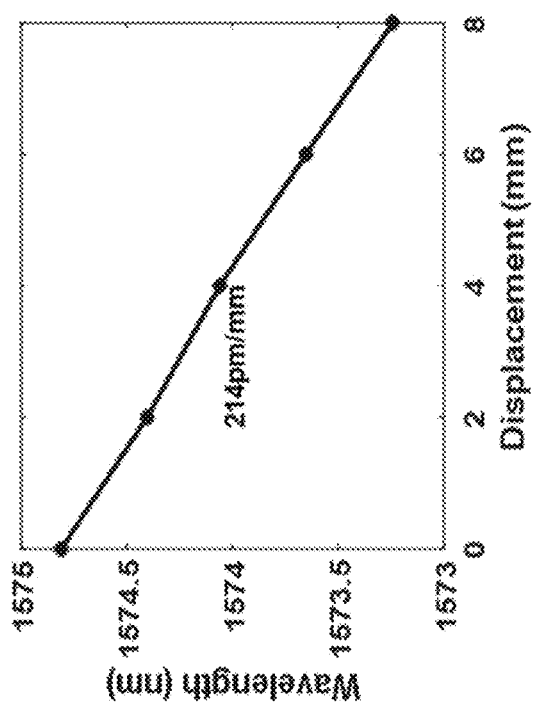
FIG. 7B is a graph of the output wavelength of an embodiment of a tunable fiber ring laser vs. the displacement of the secondary loop of said tunable fiber ring laser, in accordance with the features of the present invention.

To demonstrate the wavelength tuning capability of the fiber ring laser used in the instant invention as shown in FIGS. 1A, 2A, 4, and 5, different strains were applied on the secondary fiber loop 18 using the translation stage 20 and the spectra output by the fiber ring laser measured using an optical spectrum analyzer (OSA). The spectra are shown in FIG. 7A. The spectrum changed linearly with applied strain and a sensitivity of 214 pm/mm as shown in FIG. 7B. The output spectrum of the invented tunable fiber ring laser has a narrow linewidth (0.16 nm @3 dB) and high signal-to-noise ratio (48 dB); making it an excellent source for sensing $CO_2$ and other gasses.

Gas Sensing Material Coating Detail

To generate the multimode fiber section coated in TEOS, used in the vibration sensor shown in FIGS. 2, 4, and 5, the sol-gel dip coating method was utilized. A coreless fiber was first pulled through a tetraethoxysilane (TEOS) precursor (4.5 ml TEOS, 4.5 ml ethanol, and 1.0 ml 1.0 M HCl, rigorously stirred for 1 hour at ~50° C.) to apply the coating. The coated coreless fiber was then calcinated at a temperature of 600° C. for 1 hour to ensure the conversion of TEOS to silica. The low refractive index silica material has an improved gas absorption and provides increased interaction with the surrounding gas molecules, compared with the bare fiber surface.

Vibration Sensing Detail

Figure 8:
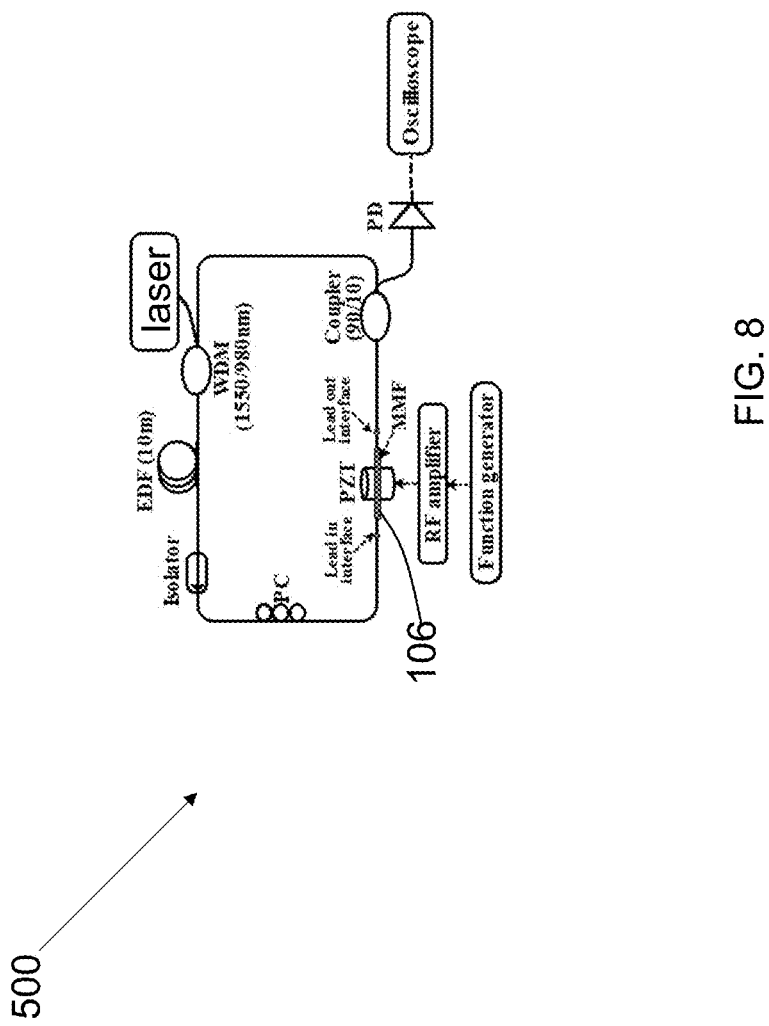
FIG. 8 is a simplified schematic of a system for measuring vibration using a tunable fiber ring laser, in accordance with the features of the present invention.
Figure 9A:
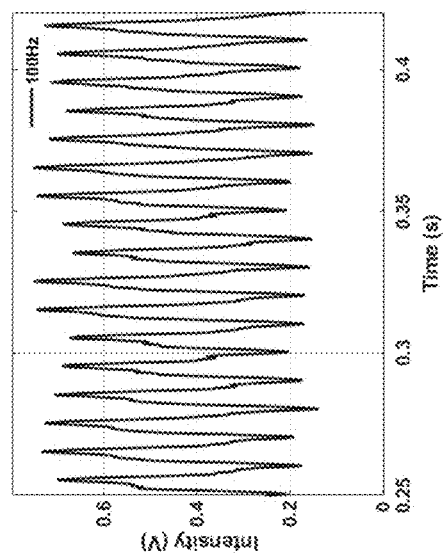
FIGS. 9A-9D show vibration data collected using the system shown in FIG. 8, FIG. 9A showing a graph of intensity vs. time data collected from a vibrational source vibrating at 100 Hz, FIG. 9B showing a graph of amplitude vs. frequency data collected from a vibrational source vibrating at 100 Hz, FIG. 9C showing a graph of intensity vs. time data collected from a vibrational source vibrating at 500 Hz, FIG. 9D showing a graph of amplitude vs. frequency data collected from a vibrational source vibrating at 500 Hz, in accordance with the features of the present invention.
Figure 9B:
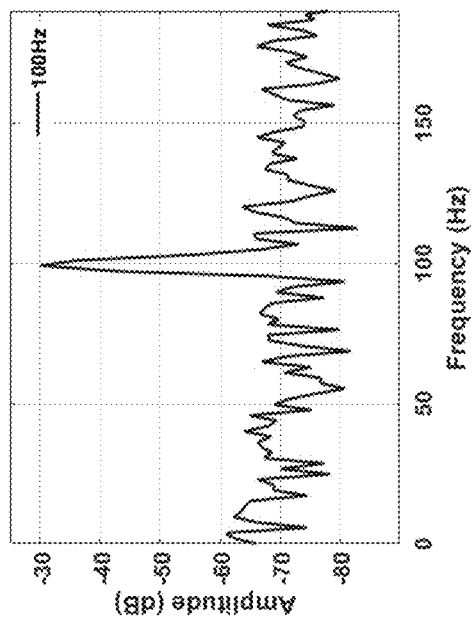
Figure 9C:
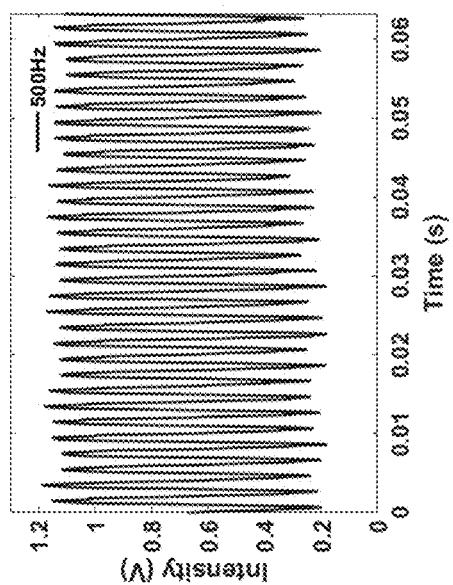
Figure 9D:
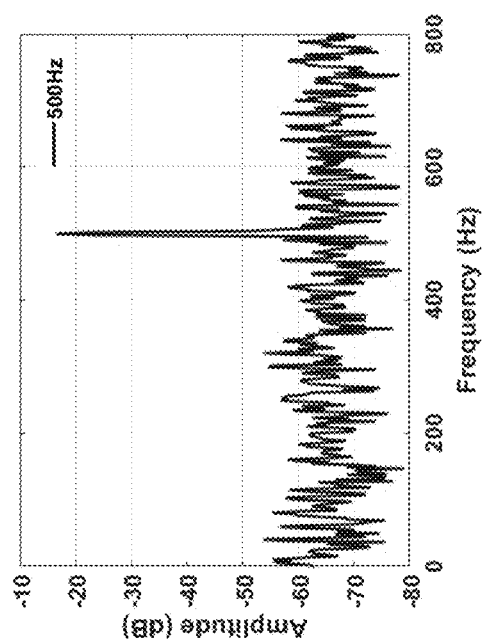

In order to demonstrate the vibration sensing capability of the invented sensor systems of FIGS. 2, 4, and 5, a simplified fiber ring laser system 500 with only a vibration sensor 106 (no gas detection sensor) as shown in FIG. 8 was fabricated using a 16 cm length of multimode fiber wrapped and glued around a piezoelectric transducer (PZT, outer diameter: 32 mm) which served as a vibration source for testing. The PZT was driven by a low-frequency RF amplifier and a waveform generator. A sinusoidal signal was generated with a fixed peak to peak amplitude of 5V over a range of frequencies. The measured time-domain signal and the corresponding frequency spectrum of 100 Hz and 500 Hz signals are illustrated in FIGS. 9A-D, respectively. The frequency spectrum was calculated using a fast Fourier transform (FFT), and exhibited a very good signal-to-noise ratio (42 dB at 500 Hz).

Simultaneous Gas Sensing and Vibration Sensing

Figure 10A:
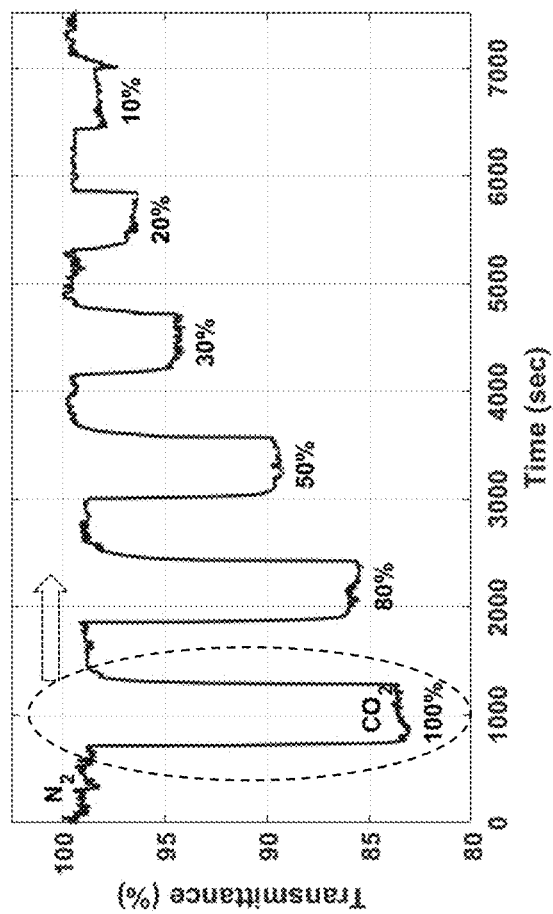
FIG. 10A is a graph showing detection data of various concentrations of $CO_2$ using the system shown in FIG. 2A at the same time that vibration was being detected, in accordance with the features of the present invention.
Figure 10B:
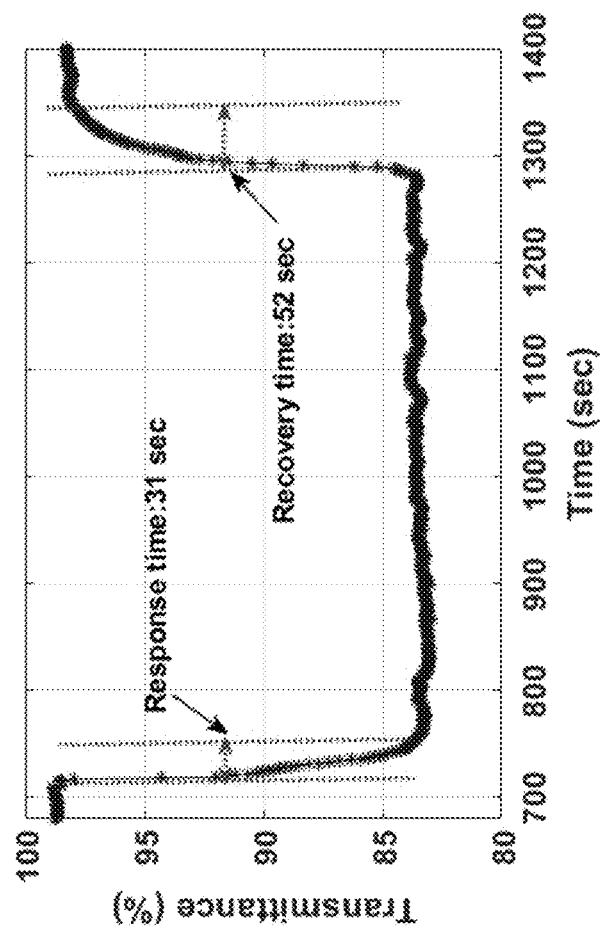
FIG. 10B is a graph showing the response and recovery times of the gas detection sensor of FIG. 2A positioned in a stream of 100% $CO_2$, in accordance with the features of the present invention.
Figure 11:
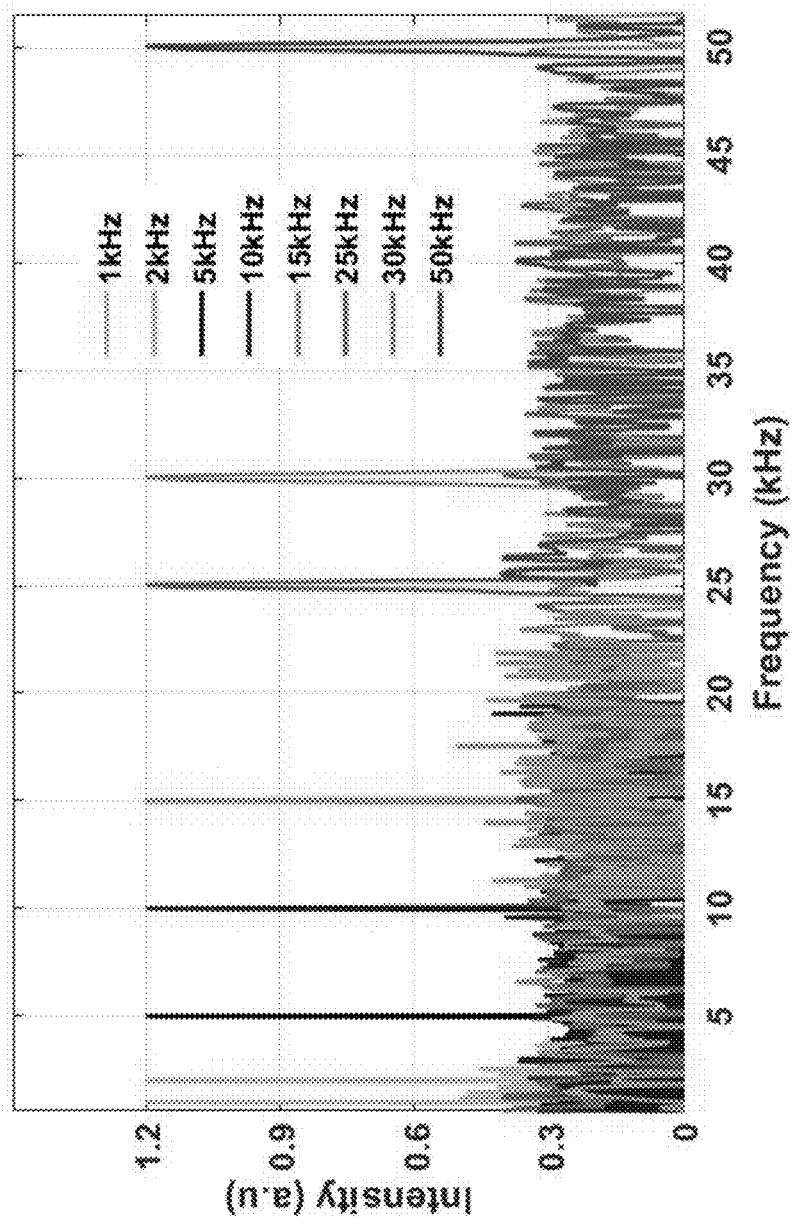
FIG. 11 is a graph of measured frequency spectra of vibration frequency signals between 1 and 50 Hz, wherein the measured frequency spectra were collected by the system shown in FIG. 2A simultaneously with the $CO_2$ detection data shown in FIG. 10A, in accordance with the features of the present invention.

The system for simultaneous sensing of a target gas and vibration sensing 100 shown in FIG. 2A was tested to demonstrate that both parameters could be tested at the same time. For this testing, $CO_2$ in $N_2$ at various concentrations was pumped into the housing 134 around the multimode fiber section 124 coated in gas sensing material 126, while the ring fiber laser 102 was outputting at the $CO_2$ absorption wavelength of 1574.6 nm. At the same time, the vibration sensor portion 106 of the system 100 was being subject to vibration of various frequencies. The transmittances at various $CO_2$ concentrations as low as 10% were measured and are illustrated in FIG. 10A. The transmittance data showed full reversibility and a linear relation versus various $CO_2$ concentration. The calculated response and recovery times of the sensor are 31 and 52 seconds, respectively, for 100% $CO_2$, as shown in FIG. 10B. Simultaneous with the gas detection measurements, the vibration sensor 106 portion of the system 100 was being subjected to vibrations at various frequencies from 1 to 50 kHz and the output spectra of the vibration sensor 106 measured. FIG. 11 shows the spectra output by the vibration sensor in response to various frequency vibrations while the gas sensor 122 portion of the system 100 was being tested at the same time. FIG. 11 demonstrates the vibration-sensing capability of the proposed invention over a wide range of frequencies.

State of the art fiber optic vibration sensors include fiber Bragg gratings (FBG) or Sagnac and Mach-Zehnder interferometers (MZI). Fabrication and processing of these state of the art sensors are difficult. Embodiments of the invented systems and methods described herein do not include or use Bragg gratings, Sagnac Interferometers, or Mach-Zehnder Interferometers.

In an embodiment the invention provides a system for simultaneously detecting vibration and the presence of a target gas comprising: a tunable fiber ring laser in electronic and optical communication with a vibration sensor and a gas detection sensor. In an embodiment, the vibration sensor comprises a length of multimode fiber extending between a first end and a second end, wherein the first and second ends of said multimode fiber are spliced to single-mode fiber. In an embodiment, the vibration sensor is configured to detect vibration having a frequency between approximately 10 Hz and approximately 400 kHz. In an embodiment, the gas detection sensor comprises a length of coreless fiber coated with a gas sensing material. In an embodiment, the gas sensing material comprises tetraethoxysilane. In an embodiment, the gas detecting sensor is configured to detect the presence of a target gas. In an embodiment, the gas detecting sensor is configured to detect a target gas present in concentrations between approximately 0.5% by volume and approximately 100% by volume surrounding the gas sensor In an embodiment, the target gas is a gas selected from the group consisting of $CO_2$, CO, $CH_4$, $H_2$, water vapor, natural gas, syngas, and combinations thereof. In an embodiment, the system is configured to detect the presence of a target gas and vibration simultaneously. In an embodiment, the system is configured to detect the presence of a target gas and vibration continuously. In an embodiment, the tunable fiber ring laser comprises a first loop of fiber placing a laser in optical communication with a second loop of fiber, wherein said second loop of fiber is positioned along the length of the fiber making up the first loop of fiber, wherein the second loop of fiber has a first end and second end, wherein the first end of the second loop of fiber is fixed in place, and wherein the second end the second loop of fiber is positioned on a translation stage.

In an embodiment, the invention provides a method for simultaneously measuring vibration and detecting the presence of a target gas in an environment comprising: providing a system for simultaneously measuring vibration and detecting a target gas into an environment; sending an optical signal to a vibration sensor and gas detection sensor; and collecting and analyzing modified signals from the vibration sensor and gas detection sensor. In an embodiment, the system is a tunable ring laser in electronic and optical communication with both a vibration sensor and a gas detection sensor. In an embodiment, sending an optical signal to the vibration sensor and gas detection sensor comprises sending an optical signal from the tunable ring laser to the vibration and gas detection sensor, causing the vibration sensor to emit a modified signal that differs from the original signal from the tunable ring laser based on the amount of vibration that is incident upon the vibration sensor, and causing the gas detection sensor to emit a modified signal that differs from the original signal from the tunable ring laser based on the amount of a target gas present around the gas detection sensor. In an embodiment, the method further comprises simultaneously measuring vibration and the presence of a target gas in the environment surrounding the system. In an embodiment, the method further comprises continuously measuring vibration and the presence of a target gas in the environment surrounding the system. In an embodiment, the frequency of the vibration detected is between approximately 10 Hz and approximately 400 kHz. In an embodiment, the gas is present in the environment in a concentration between approximately 0.5% vol and approximately 100% vol.

Having described the basic concept of the embodiments, it will be apparent to those skilled in the art that the foregoing detailed disclosure is intended to be presented by way of example. Accordingly, these terms should be interpreted as indicating that insubstantial or inconsequential modifications or alterations and various improvements of the subject matter described and claimed are considered to be within the scope of the spirited embodiments as recited in the appended claims. Additionally, the recited order of the elements or sequences, or the use of numbers, letters or other designations therefor, is not intended to limit the claimed processes to any order except as may be specified. All ranges disclosed herein also encompass any and all possible sub-ranges and combinations of sub-ranges thereof. Any listed range is easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as up to, at least, greater than, less than, and the like refer to ranges which are subsequently broken down into sub-ranges as discussed above. As utilized herein, the terms "about," "substantially," and other similar terms are intended to have a broad meaning in conjunction with the common and accepted usage by those having ordinary skill in the art to which the subject matter of this disclosure pertains. As utilized herein, the term "approximately" shall carry the meaning of being within 15, 10, 5, 4, 3, 2, or 1 percent of the subject measurement, item, unit, or concentration, with preference given to the percent variance. It should be understood by those of skill in the art who review this disclosure that these terms are intended to allow a description of certain features described and claimed without restricting the scope of these features to the exact numerical ranges provided. Accordingly, the embodiments are limited only by the following claims and equivalents thereto. All publications and patent documents cited in this application are incorporated by reference in their entirety for all purposes to the same extent as if each individual publication or patent document were so individually denoted.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

What is claimed is:

1. A method for simultaneously measuring vibration and detecting the presence of a target gas in an environment comprising:
   providing a system for simultaneously measuring vibration and detecting a target gas into an environment, wherein the system is a tunable ring laser in electronic and optical communication with both a vibration sensor and a gas detection sensor;
   sending an optical signal to a vibration sensor and gas detection sensor, wherein sending an optical signal to the vibration sensor and gas detection sensor comprises sending an optical signal from the tunable ring laser to the vibration and gas detection sensor, causing the vibration sensor to emit a modified signal that differs from the original signal from the tunable ring laser based on the amount of vibration that is incident upon the vibration sensor, and causing the gas detection sensor to emit a modified signal that differs from the original signal from the tunable ring laser based on the amount of a target gas present around the gas detection sensor; and
   collecting and analyzing modified signals from the vibration sensor and gas detection sensor.

2. The method of claim 1 further comprising simultaneously measuring vibration and the presence of a target gas in the environment surrounding the system.

3. The method of claim 1 further comprising continuously measuring vibration and the presence of a target gas in the environment surrounding the system.

4. The method of claim 1 wherein the frequency of the vibration detected is between approximately 10 Hz and approximately 400 KHz.

5. The method of claim 1 wherein the gas is present in the environment in a concentration between approximately 0.5% vol and approximately 100% vol.

\* \* \* \* \*